United States Patent [19]

Drake

[11] 4,117,002

[45] Sep. 26, 1978

[54] PYROLYSIS OF HEAVIES FORMED IN PRODUCTION OF UNSATURATED DINITRILES

[75] Inventor: Charles A. Drake, Nowata, Okla.

[73] Assignee: Phillips Petroleum Company, Bartlesville, Okla.

[21] Appl. No.: 813,062

[22] Filed: Jul. 5, 1977

[51] Int. Cl.² .................. C07C 120/00; C07C 121/20; C07C 121/70

[52] U.S. Cl. ........................... 260/465.8 R; 260/464; 260/465 H; 260/465.3; 260/465.9

[58] Field of Search ............... 260/465.9, 464, 465 K, 260/465.8 R, 465 H

[56] References Cited

U.S. PATENT DOCUMENTS

| | | | |
|---|---|---|---|
| 2,407,848 | 9/1946 | Ray | 260/465.9 |
| 2,641,607 | 6/1953 | Albisetti et al. | 260/465.9 |
| 3,247,237 | 4/1966 | Hagemeyer, Jr. | 260/465.9 |
| 3,840,583 | 10/1974 | Turk et al. | 260/465.8 R |
| 3,883,606 | 5/1975 | Banks | 260/465.9 X |
| 3,898,268 | 8/1975 | Drake | 260/465.9 |
| 3,929,860 | 12/1975 | Drake | 260/465.9 |
| 3,985,786 | 10/1976 | Drake | 260/465.9 K |
| 3,996,262 | 12/1976 | Turk et al. | 260/465.9 |
| 4,001,294 | 1/1977 | Drake et al. | 260/465.9 X |
| 4,021,465 | 5/1977 | Fozzard et al. | 260/465.8 R |

OTHER PUBLICATIONS

Burlant et al.; J. Polymer Science, XVII, pp. 249–256, (1956).
Takayama; C.A., 55 (1961), 17073f.
Brandrup et al.; Polymer Handbook, (1966), Interscience, pp. V–5–V–11.

*Primary Examiner*—Joseph Paul Brust

[57] ABSTRACT

An olefinically unsaturated mononitrile is reacted with a monoadduct of an olefinically unsaturated mononitrile and an olefinically unsaturated hydrocarbon compound to produce a dinitrile product and at least one undesired compound having a higher boiling point than the dinitrile product. The undesired compound is separated from the dinitrile product and subjected to pyrolysis conditions to decompose at least a portion thereof to olefinically unsaturated mononitrile, olefinically unsaturated hydrocarbon compound, and monoadduct, which can be recovered and recycled to the dinitrile synthesis.

28 Claims, 1 Drawing Figure

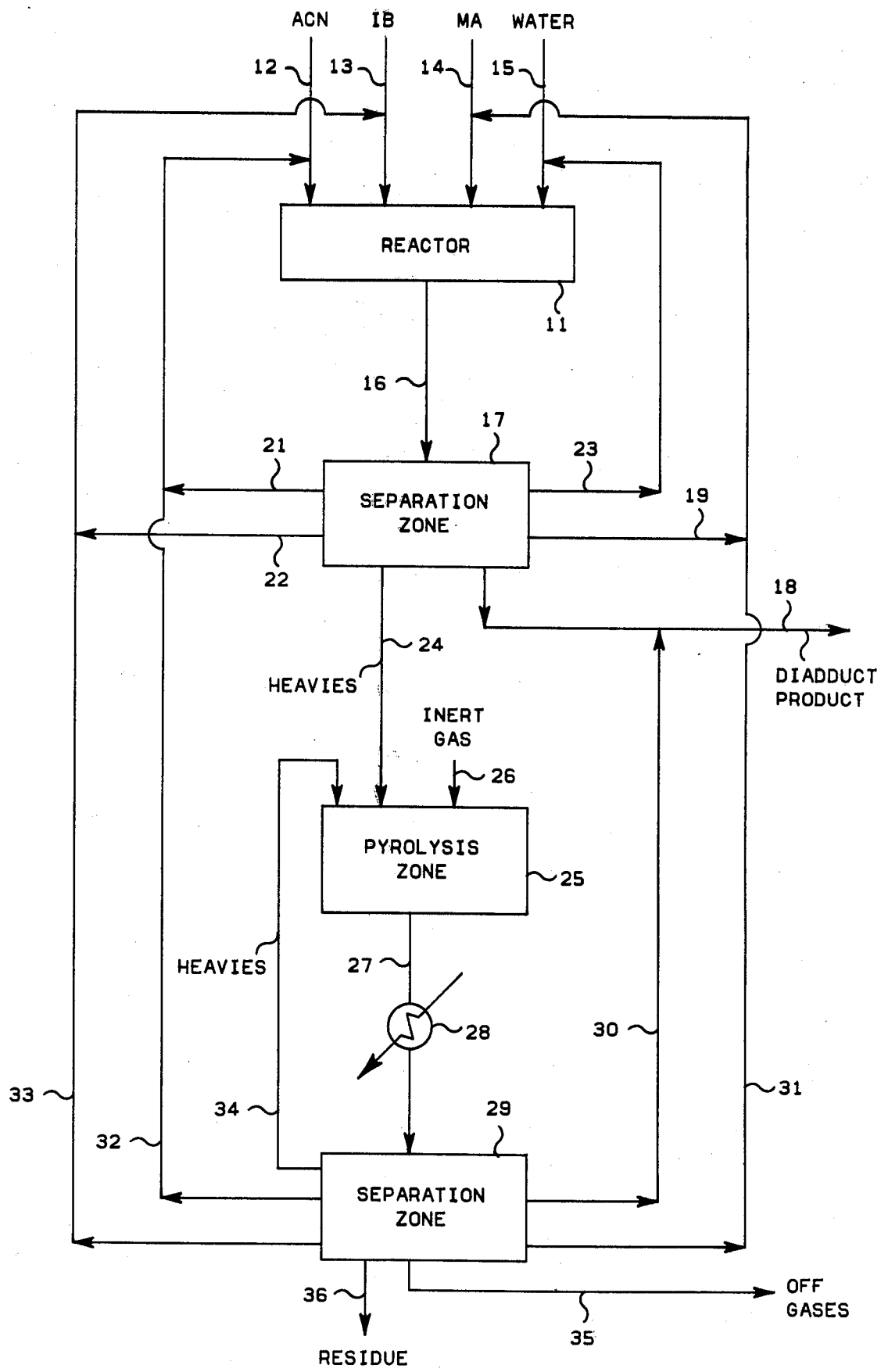

PYROLYSIS OF HEAVIES FORMED IN PRODUCTION OF UNSATURATED DINITRILES

This invention relates to the production of unsaturated dinitriles. In a specific aspect the invention relates to the pyrolysis of the undesirable heavy byproducts or heavies to recover starting materials.

U.S. Pat. No. 3,840,583 of S. D. Turk and C. A. Drake describes the preparation of olefinically unsaturated dinitriles (diadduct) from an olefin, an unsaturated mononitrile, and a monoadduct reaction product of the olefin and the mononitrile. In particular, the use of acrylonitrile and isobutylene in the reaction scheme of said patent provides a route to unsaturated $C_{10}$ dinitriles which can be hydrogenated to saturated $C_{10}$ diamines. The saturated diamine products have found utility in a number of areas including the preparation of fiber grade polyamides from the reaction of said diamines with terephthalic acid, as disclosed in U.S. Pat. No. 3,980,621 of Robert W. Campbell and H. Wayne Hill, Jr. In addition, U.S. Pat. No. 3,985,786 of C. A. Drake discloses a single-stage process for the preparation of the unsaturated dinitriles (diadduct) by the reaction of unsaturated mononitrile with suitable olefin in the presence of water and the monoadduct reaction product of the nitrile and the olefin.

In the production of diadduct according to the procedures of the above described patents, it has been found that in the purification of the crude diadduct by fractional distillation a significant portion of the crude diadduct remains as kettle residues or heavies. A conventional method of disposing of organic distillation heavies is to burn the heavies in the process for their fuel value. However, because of the nitrogen content of the heavies in this instance, it is possible that environmental regulations may prevent this method of disposal from being employed at all or at least for very large amounts of the material. It is also obvious that the amount of heavies produced in the production of the unsaturated dinitriles represents a loss of starting olefin and unsaturated mononitrile which is not recovered in the purified unsaturated dinitriles.

Accordingly, it is an object of the present invention to reduce the amount of heavies which must ultimately be subjected to disposal. Another object of the invention is to recover economically valuable products from the heavies. It is an object of the invention to improve the economic feasibility of a process for the production of unsaturated dinitriles. Yet another object is to improve the yield of desired products. A further object of the invention is to provide a new and improved process for the production of unsaturated dinitriles. Other objects, aspects and advantages of the invention will be apparent from a study of the specification, the drawing and the appended claims to the invention.

In accordance with the present invention, the diadduct heavies are subjected to pyrolysis to thermally crack at least a portion of the heavies into the starting materials and/or other useful materials. The starting materials can be recycled to the diadduct formation process.

The present invention is applicable to both the two-stage process and the single-stage process for the production of the unsaturated dinitriles; however the single-stage process is preferred and the detailed description will be in terms of a single-stage process for the production of diadduct. In the single-stage process, an unsaturated mononitrile, e.g. acrylonitrile, is reacted with an olefinic hydrocarbon compound, e.g. isobutylene, to produce unsaturated mononitriles (monoadduct) having a greater number of carbon atoms, e.g. 5-methyl-5-hexenenitrile. The monoadduct can be recovered and passed to the second stage wherein the unsaturated dinitriles (diadduct), e.g. 5-methylenenonanedinitrile and 5-methyl-4-nonenedinitrile, are formed by the monoaddition of an unsaturated mononitrile, e.g. acrylonitrile, and a monoadduct reaction product. In the single-stage process, an unsaturated mononitrile and an olefinic hydrocarbon compound are introduced into a reactor, preferably along with monoadduct, to form monoadduct and diadduct in the single reactor. The reaction effluent of the single stage or from the second stage of the two-stage process can be separated into diadduct product, unreacted monoadduct, unreacted unsaturated mononitrile, unreacted olefinic hydrocarbon compound, and diadduct heavies. Small amounts of dimers of the unsaturated mononitrile may also be present. The unreacted monoadduct and the unreacted unsaturated mononitrile can be recycled to the appropriate stage. The heavies can be subjected to pyrolysis in accordance with the present invention and the unsaturated mononitrile, olefinic compound, and monoadduct recovered from the pyrolysis effluent can be recycled to the appropriate reaction stage.

In the drawing, the single FIGURE is a diagrammatic illustration of a single-stage reaction process for the production of unsaturated dinitriles which embodies the present invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, non-conjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

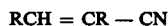

wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl, alkaryl, and arylcycloalkyl radicals. Examples of unsaturated nitriles meeting the requirements of the above formula are acrylonitrile, methacrylonitrile, 2-decenenitrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures of any two or more thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $R'_2C = CR' - CHR'_2$, wherein each R' is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4,-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures of any two or more thereof.

Suitable monoadduct reactants include any monoadduct reaction product of an olefinic hydrocarbon, as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

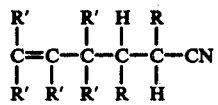

wherein R and R' are as defined hereinabove. Generally a lesser amount of an isomeric monoadduct reaction product having the formula

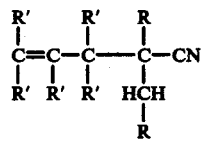

wherein R and R' are as defined hereinabove, is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the "ene" reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile, the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4-t-butyl-5-methyl-5-hexenenitrile. Other factors not fully understood at present may influence the relative amounts of the possible isomers in the monoadduct reaction product. The isomeric mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2-(n-butyl)-4-pentenenitrile, 2-(n-butyl)-5-phenyl-4-pentenenitrile, and mixtures of any two or more thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture containing as the major isomer species 5-methylenenonanedinitrile and 5-methyl-4-nonenedinitrile, and containing the minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the production of the diadduct reaction products. In general the mol ratio of olefinically unsaturated mononitrile reactant to olefinic hydrocarbon reactant will be in the range of about 10:1 to about 0.1:1, preferably in the range of about 5:1 to about 0.2:1, and more preferably in the range of about 2:1 to about 0.3:1. In a single step process the monoadduct reaction product will generally be employed in an amount such that during substantially the entire reaction period the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction to the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it will be generally preferred for them to be the same. The total reaction mixture includes all fluid materials present in the reaction zone, i.e. reactants, diluents, products, byproducts, etc.

Any suitable reaction conditions for either a batch process or a continuous process can be employed in the production of the diadduct reaction products. The reaction time employed can vary widely. Generally a time period of from about 2 minutes to about 48 hours, preferably from about 30 minutes to about 10 hours, and more preferably from about 1 hour to about 5 hours is an adequate period of time for olefin, unsaturated mononitrile and a monoadduct reaction product to be suitably admixed in the preparation of reaction products in high yields in a single-stage batch process. In a continuous single-stage process the liquid hourly space velocity will generally be in the range of about 0.05 to about 20, preferably in the range of about 0.1 to about 10, more preferably in the range of about 0.5 to about 2.

The reaction temperatures that can be employed can vary widely. Generally, however, suitable reaction temperatures for the single-stage reaction are within the range of about 100° C. to about 500° C., and preferred reaction temperatures are within the range of about 200° C. to about 350° C.

The reaction pressures suited to the practice of this invention also vary widely. Reaction pressure within a range of about atmospheric pressure to about 689.47 MPa (100,000 psig) can be employed in the single stage process; however, reaction pressures within the range of about 3.45 MPa (500 psig) to about 27.58 MPa (4000 psig) are preferably employed.

If desired, the production of the diadduct can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amount in the range of about 0.001 to about 5, preferably in the range of about 0.1 to about 1, percent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butylcatechol, para-hydroxydiphenylamine, and the like, and combinations of any two or more thereof.

The reaction of the above described olefinic hydrocarbon reactant, olefinically unsaturated mononitrile reactant and monoadduct reaction product reactant is preferably carried out in the presence of a diluent. While any suitable diluent can be employed, the presently preferred diluent is an aqueous diluent comprising at least 50 weight percent water, more preferably at least 80 weight percent water, and more preferably consisting essentially of water. The codiluent, if employed, can be any solvent or diluent which is nonreactive with either the reactants or the reaction products. Examples of other suitable diluents which can be employed alone or as codiluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and the like, and mixtures of any two or more thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone.

The amount of diluent currently preferred is in the range of about 0.1 to about 20 parts by weight of total diluent per part by weight of olefinically unsaturated mononitrile reactant charged to the reaction zone. The advantages of the aqueous diluent system include improved selectivity to the desired olefinically unsaturated dinitrile and reduced amounts of heavy polymeric byproduct. This latter byproduct is particularly objectionable because it tends to foul reactor surfaces.

A convenient method of carrying out this invention comprises heating a mixture of an olefinically unsaturated mononitrile (e.g. acrylonitrile), an olefinic hydrocarbon (e.g. isobutylene), and a monoadduct reaction product reactant (e.g. a mixture of 5-methyl-5-hexenenitrile and 2,4-dimethyl-4-pentenenitrile) in a reaction pressure vessel at a temperature within the range of about 240° C. to about 350° C. and at a pressure in the range of about 3.45 to about 27.58 MPa (about 500 to about 4000 psig); the mol ratio of the olefinically unsaturated mononitrile to the olefinic hydrocarbon being in the range of about 5:1 to about 0.2:1; and the concentration of the monoadduct reaction product reactant in the reaction mixture being in the range of about 20 to about 80 weight percent. Thereafter, the resulting olefinically unsaturated dinitrile reaction product is readily isolated from the reaction effluent mixture by any convenient product recovery method, such as fractional distillation. Any suitable temperatures and pressures can be employed in a single batch fractional distillation zone or in a plurality of fractional distillation zones operated in batch or continuous operation in any desired sequence. However, low temperatures and subatmospheric pressures are desirable to avoid polymerization and/or thermal degradation of the desirable materials. In general the fractional distillation temperatures will be in the range of about 15° to about 350° C., and preferably in the range of about 25° to about 250° C., while the fractional distillation pressures will generally be in the range of about 0.01 kPa to about 110 kPa and preferably will be in the range of about 0.1 kPa to about 100 kPa. The reaction effluent mixture can be readily separated by fractional distillation into a diluent stream, an unreacted olefinically unsaturated mononitrile (e.g. acrylonitrile) stream, an unreacted olefinic hydrocarbon compound (e.g. isobutylene) stream, a monoadduct reactant (e.g. a mixture of 5-methyl-5-hexenenitrile and 2,4-dimethyl-4-pentenenitrile) stream, a diadduct (e.g. a mixture of olefinically unsaturated $C_{10}$ dinitriles) stream, and a diadduct heavies stream. The diadduct heavies constitute that portion of the reaction effluent mixture which has a boiling point significantly higher than the diadduct. In the one-step synthesis of diadduct from acrylonitrile, isobutylene and monoadduct of acrylonitrile and isobutylene, the reaction effluent contains isobutylene, acrylonitrile, monoadduct, α-methyleneglutaronitrile, trans-1,2-dicyanocyclobutane, cis-1,2-dicyanocyclobutane, diadduct, and diadduct heavies, listed in the order of increasing boiling points. Isobutylene (boiling point: 6° C. at 760 mm) and acrylonitrile (boiling point: 78°–79° C. at 760 mm) can be readily separated by simple fractionation and recycled to the diadduct synthesis reaction. Fractional distillation of acrylonitrile at low pressure and temperature is advantageous in minimizing polymerization of the acrylonitrile. Recovery of monoadduct (boiling point of about 120° C. at 125 mm) for recycle can be accomplished by fractional distillation of the monoadduct from the small amounts of α-methyleneglutaronitrile (boiling point:

140° C. at 16 mm) and trans-1,2-dicyanocyclobutane (boiling point: 122° C. at 6 mm). After removal of the monoadduct and the two light boiling dimers, the resulting kettle product can be introduced into another fractional distillation column for the separation of the diadduct from the heavies. Elaborate fractionation is not required for this latter separation, but relatively low pressure is desirable in order to minimize thermal degradation of the diadduct (boiling point: 176° C. at 10 mm, 192° C. at 20 mm). Small amounts of close boiling cis-1,2-dicyanocyclobutane are generally taken overhead with the diadduct, but the products of hydrogenation of this byproduct are readily separated from the diamines obtained by hydrogenation of the diadduct.

In the process employing acrylonitrile, isobutylene and the monoadduct thereof, the diadduct heavies are black-brown, extremely viscous and tacky materials at 23° C., and can be characterized by the observation that approximately 90 weight percent of the heavies are not distillable at 0.0133 kPa and 320° C. A typical sample of the diadduct heavies produced in a process for the production of diadduct from acrylonitrile and isobutylene and the monoadduct thereof showed the following analysis in terms of elemental content: 75.2 weight percent carbon, 8.4 weight percent hydrogen, and 15.7 weight percent nitrogen. Molecular weight analysis indicated an average molecular weight of 629. Infrared analysis of the diadduct heavies indicated the presence of a secondary amine function as well as the nitrile functional group. The material also contained a small amount of olefinic unsaturation. Nuclear magnetic resonance (NMR) analysis of the diadduct heavies did not detect any aromatic protons in the material and further indicated that the secondary amine function was evidently a minor component of the material and further confirmed the low concentration of the olefinic unsaturation in the material. Although, on occasion, dimers of acrylonitrile have been recovered, dimers and trimers of isobutylene have not been detected in the diadduct synthesis reaction effluent. The above analyses taken together indicated that the diadduct heavies probably represent an oligomer (tetramer) of the diadduct which had polymerized through the olefinic unsaturation in the diadduct, and small amounts of an oligomer or low molecular weight polymer of acrylonitrile. Since the diadduct itself is a mixture of isomeric unsaturated dinitriles having 10 carbon atoms per molecule, it is very likely that the tetramers are a complex mixture of isomeric materials. Such a tetramer of the diadduct would contain forty carbon atoms and eight nitrile and/or amine functions per molecule. In general the oligomers of the diadduct are complex, high molecular weight materials having at least four nitrile and/or amine functions per molecule.

Any suitable temperature, pressure, and reaction time can be employed in the pyrolysis of the diadduct heavies. In general the pyrolysis temperature will be in the range of about 450° to about 1000° C., preferably in the range of about 500° to about 900° C., and more preferably in the range of about 500° to about 700° C. The pressure in the pyrolyzing reaction zone will generally be in the range of about 1 kPa to about 1000 kPa, preferably in the range of about 25 kPa to about 200 kPa, and more preferably in the range of about 50 kPa to about 120 kPa. While the pyrolysis can be conducted as a batch reaction for a suitable time, e.g. in the range of about 5 minutes to about 10 hours, it will preferably be as a continuous process. The liquid hourly space velocity (LHSV) for a continuous pyrolysis reaction will generally be in the range of about 0.1 to about 10, preferably in the range of about 0.5 to about 2, volumes of liquid feed per hour per volume of pyrolysis reaction zone.

If desired an inert gas such as nitrogen, carbon dioxide, helium, argon, and the like, or a mixture thereof, can be passed through the pyrolysis reaction zone in order to effectively sweep the pyrolysis products from the reaction zone to prevent subsequent side reactions of the desired products under the high temperatures employed in the reaction zone. The inert gas stream can be employed at any suitable rate, but will generally be utilized at a gas hourly space velocity (GHSV) in the range of about 1 to about 500, preferably in the range of about 5 to about 100, standard volumes of inert gas per hour per volume of the pyrolysis reaction zone.

As is conventional in most pyrolysis reactions, the process of the present invention preferably employs particulate materials in the pyrolysis reaction zone having a high surface area and an ability to transfer heat from the reaction zone to the feed material. For example, quartz chips, stainless steel chips, refractory oxides of various types including alumina, thoria, titania, and the like, and admixtures of any two or more thereof, can be utilized as the heat transfer material in the pyrolysis reaction zone. Such particulate materials can be in any of a variety of shapes and sizes, such as beads, chips, pellets, shavings, and the like, as well as mixtures of any two or more thereof.

In order to recover the valuable pyrolysis products obtained according to the present invention, the effluent from the pyrolysis reaction zone can be passed to suitable recovery and separation means, e.g. one or more condensation traps or zones maintained at a relatively low temperature can be employed in order to collect the products. If more than one condensation trap or zone is employed, it is possible to maintain different temperatures in the condensation zones in order to selectively condense products from the pyrolysis reaction zone. It is also possible to employ a single condensation zone in order to trap essentially all of the products of the pyrolysis. The material collected in the condensation zone or zones can then be fractionally distilled to separate the products of the pyrolysis into relatively pure streams. For example, in the case of diadduct heavies obtained from acrylonitrile and isobutylene as the starting materials, the fractional distillation of the pyrolysis effluent lected in the condensation zone can result in the recovery of relatively pure streams of each of acrylonitrile, isobutylene, monoadduct and diadduct. It is, of course, possible to recycle any of the first three materials to the appropriate process steps for the conversion of acrylonitrile and isobutylene into monoadduct and diadduct. It is also possible to recycle any remaining diadduct heavies to the pyrolysis zone for further conversion according to the instant invention, while withdrawing from the process any residue char and/or light gaseous products.

Referring now to the drawing, an embodiment involving a continuous process for the reaction of acrylonitrile, isobutylene and a monoadduct of acrylonitrile and isobutylene to produce 5-methylenenonanedinitrile and 5-methyl-4-nonenedinitrile will be described. Acrylonitrile and isobutylene are introduced into single-stage reactor 11 by way of conduit means 12 and 13, respectively. A monoadduct of acrylonitrile and isobutylene, i.e. predominately 5-methyl-5-hexenenitrile with a small amount of 2,4-dimethyl-4-pentenenitrile, is introduced into reactor 11 by way of conduit means 14, while water is introduced into reactor 11 by way of conduit means 15. A convenient method of carrying out the production of the diadduct in reactor 11 comprises heating the mixture of acrylonitrile, isobutylene, and the mixture of 5-methyl-5-hexenenitrile and 2,4-dimethyl-4-pentenenitrile in a reaction pressure vessel at a temperature within the range of about 240° to about 350° C. and at pressures in the range of about 3.45 to about 27.58 MPa (about 500 to about 4000 psig), the mol ratio of the acrylonitrile to the isobutylene being in the range of about 5:1 to about 0.2:1, and the concentration of the monoadduct reactant in the reaction mixture being in the range of about 20 to about 80 weight percent.

The reaction effluent is withdrawn from reactor 11 and passed by way of conduit means 16 to a suitable separation zone 17. A relatively pure diadduct product stream comprising 5-methyl-4-nonenedinitrile and 5-methylenenonanedinitrile and small amounts of other $C_{10}$ olefinically unsaturated dinitriles is withdrawn from separation zone 17 and from the process by way of conduit means 18. A relatively pure monoadduct stream comprising 5-methyl-5-hexenenitrile and 2,4-dimethyl-4-pentenenitrile is withdrawn from separation zone 17 and is recycled to reactor 11 by way of conduit means 19 and 14. Similarly an acrylonitrile stream, an isobutylene stream and a water stream are withdrawn from separation zone 17 and passed by way of conduit means 21 and 12, 22 and 13, and 23 and 15, respectively, to reactor 11. The remainder of the reaction effluent from reactor 11 is withdrawn from separation zone 17 by way of conduit means 24 as a diadduct heavies stream and is introduced into pyrolysis zone 25. Pyrolysis zone 25 is filled with high surface area particulate heat transfer material and is heated to a temperature in the range of about 500° to about 700° C. An inert gas is introduced into pyrolysis zone 25 through conduit means 26 to flush the pyrolysis products from zone 25 through outlet conduit means 27, containing cooling means 28, into separation zone 29. A relatively pure diadduct product stream is recovered from separation zone 29 and passed by way of conduit means 30 into conduit means 18. A relatively pure monoadduct stream is recovered from separation zone 29 and passed through conduit means 31 and 14 to reactor 11. An acrylonitrile stream and an isobutylene stream are passed from separation zone 29 through conduit means 32 and 12 and 33 and 13, respectively, to reactor 11. A stream containing unreacted and/or relatively unreacted heavies can be passed through conduit means 34 from separation zone 29 to pyrolysis zone 25. An off-gas stream comprising inert gas and light gaseous cracked products is withdrawn from separation zone 29 by way of conduit means 35 for disposal or utilization, e.g. as a fuel gas. A residue stream containing carbon, char and very high molecular weight material is withdrawn from separation zone 29 and from the process by way of conduit means 36.

The following examples are presented in further illustration of the invention and should not be construed in undue limitation thereof.

EXAMPLE I

A quartz tube of 2.6 cm outside diameter and 51 cm in length was filled with quartz chips. A 6-gram sample of the diadduct heavies obtained as the fraction having a boiling point higher than the diadduct in the fractional distillation of the crude diadduct product obtained from acrylonitrile and isobutylene was placed in the tube and subjected to non-catalytic pyrolysis reaction conditions comprising a temperature of about 500° C. at atmospheric pressure with a strong flow of nitrogen gas passing upwardly through the tube. The reaction effluent was withdrawn from the tube and passed to a cold trap maintained at about −70° C. by use of a slurry of solid carbon dioxide (dry ice) and acetone. After about 13–30 minutes operation at about 500° C., there was obtained about 1 ml of liquid product in the cold trap. The liquid product was analyzed by gas-liquid phase chromatography which indicated the presence of acrylonitrile, isobutylene and monoadduct in the liquid product collected. There was obtained about 10% by weight isobutylene, about 10% by weight monoadduct, about 60% by weight acrylonitrile, and about 20% by weight of higher boiling material. Thus about 80% by weight of the liquid product produced by the pyrolysis reaction was useful for recycling as reactants to the process for producing the diadduct.

A previous analysis of the diadduct heavies dissolved in acetone by gas-liquid phase chromatography had indicated no acrylonitrile, monoadduct or acrylonitrile dimer was present in the diadduct heavies. However, a small amount of diadduct was noted in the sample analyzed.

The above results indicate that diadduct heavies obtained during the production of a $C_{10}$ unsaturated dinitrile by the reaction of acrylonitrile and isobutylene can be pyrolyzed to provide substantial quantities of the starting materials, acrylonitrile and isobutylene, as well as the monoadduct of said starting materials.

EXAMPLE II

A steel pipe reactor of 1.3 cm outside diameter and 51 cm in length was filled with 60 ml of a silica-alumina particulate material of the following composition: 95% gamma alumina, 4% silica, 0.3% magnesium oxide and 0.3% ferric oxide ($Fe_2O_3$). The above described reactor was heated to 550° C. at atmospheric pressure in a furnace with a stream of nitrogen passing at 1 standard cubic foot per hour (472 GHSV) through the reaction zone. Diadduct heavies obtained from the distillation of crude diadduct prepared from acrylonitrile and isobutylene was pumped through the reactor at a rate of 1 ml per minute (1 LHSV). It was necessary to apply heat to the crude diadduct pump system in order to keep the material fluid enough to pass through the pump into the reactor. Effluent from the reactor was collected in a cold trap, described in Example I, for a period of 30 minutes. During this time, about 20 ml of liquid material was collected in the cold trap. The liquid material was analyzed as in Example I by gas-liquid phase chromatography which indicated the following composition: isobutylene about 10% by weight, acrylonitrile about 30% by weight, monoadduct about 10% by weight, diadduct about 5% by weight, about 25% by weight heavies, and about 20% by weight of unidentified material having a volatility greater than that of the heavies. Thus about 50% by weight of the liquid product of the pyrolysis reaction was useful for recycling as reactants to the process for producing the diadduct. It is possible that at least a portion of the diadduct recovered in the effluent from the pyrolysis reaction zone was present initially in the diadduct heavies feed.

The results described above indicate that diadduct heavies obtained during the production of unsaturated $C_{10}$ dinitriles from the reaction of acrylonitrile and isobutylene can be pyrolyzed to recover significant quantities of starting materials, isobutylene and acrylonitrile, as well as intermediates in the process.

Reasonable variations and modifications are possible within the scope of the foregoing disclosure, the drawing and the appended claims to the invention.

I claim:
1. A process which comprises reacting (a) at least one olefinically unsaturated mononitrile reactant and (b) at least one monoadduct of an olefinic hydrocarbon compound and an olefinically unsaturated mononitrile compound under reaction conditions suitable to produce at least one desired olefinically unsaturated dinitrile product and at least one undesired compound having a higher boiling point than said at least one desired olefinically unsaturated dinitrile product, each of said olefinically unsaturated mononitrile reactant and said olefinically unsaturated mononitrile compound containing a cyano group attached to a carbon atom adjacent and doubly bonded to a carbon atom which is attached to at least one hydrogen atom, said olefinic hydrocarbon compound having at least one olefinic linkage having joined to one of the doubly bonded carbons thereof a carbon atom having at least one hydrogen atom attached thereto;
  separating the resulting reaction effluent to produce a first fraction comprising said at least one desired olefinically unsaturated dinitrile product and a second fraction comprising said at least one undesired compound;
  subjecting said second fraction to pyrolysis conditions to decompose at least a portion of said at least one undesired compound to thereby produce a decomposition product comprising at least one of said at least one olefinically unsaturated mononitrile reactant, said at least one monoadduct, said olefinic hydrocarbon compound and said olefinically unsaturated mononitrile compound; and
  recovering said decomposition product from the resulting pyrolysis effluent.

2. A process in accordance with claim 1 wheren said at least one undesired compound comprises an oligomer of the reaction product of said monoadduct and said olefinically unsaturated mononitrile reactant.

3. A process in accordance with claim 2 wherein said pyrolysis conditions comprise a temperature in the range of about 450° to about 1000° C.

4. A process in accordance with claim 3 wherein said pyrolysis conditions further comprise a pressure in the range of about 1 kPa to about 1000 kPa.

5. A process in accordance with claim 4 wherein said pyrolysis conditions further comprise a reaction time in the range of about 5 minutes to about 10 hours for a batch pyrolysis reaction or a liquid hourly space velocity in the range of about 0.1 to about 10 for a continuous pyrolysis reaction.

6. A process in accordance with claim 5 further comprising recycling at least a portion of the thus recovered decomposition product to the step of reacting said at least one olefinically unsaturated mononitrile reactant with said monoadduct.

7. A process in accordance with claim 6 wherein said mononitrile reactant is acrylonitrile, said mononitrile compound is acrylonitrile and said olefinic hydrocarbon compound is isobutylene.

8. A process in accordance with claim 1 further comprising recyling at least a portion of the thus recovered decomposition product to the step of reacting said at least one olefinically unsaturated mononitrile reactant with said monoadduct.

9. A process in accordance with claim 8 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

10. A process in accordance with claim 1 wherein said pyrolysis reaction conditions comprise a temperature in the range of about 500° to about 900° C. and a pressure in the range of about 25 kPa to about 200 kPa.

11. A process in accordance with claim 1 wherein said mononitrile reactant is acrylonitrile, said mononitrile compound is acrylonitrile, and said olefinic hydrocarbon compound is isobutylene.

12. A process in accordance with claim 11 wherein acrylonitrile and said monoadduct are recovered from said pyrolysis effluent and recycled to the step of reacting acrylonitrile and monoadduct.

13. A process in accordance with claim 1 wherein each of said at least one olefinic hydrocarbon compound, said at least one olefinically unsaturated mononitrile reactant and said at least one olefinically unsaturated mononitrile compound is free of acetylenic unsaturation and has from 3 to 18 carbon atoms per molecule with from 1 to 2 ethylenically unsaturated, nonconjugated double bonds as the sole aliphatic unsaturation.

14. A process in accordance with claim 13 wherein each said olefinic hydrocarbon compound is represented by the formula $R'_2C=CR'-CHR'_2$, wherein each R' is independently selected from the group consisting of hydrogen and hydrocarbyl radicals; and wherein each of said at least one olefinically unsaturated mononitrile reactant and said olefinically unsaturated mononitrile compound is represented by the formula $RCH=CR-CN$ wherein each R is independently selected from the group consisting of hydrogen and hydrocarbyl radicals.

15. A process in accordance with claim 14 wherein said decomposition product comprises said mononitrile reactant and said monoadduct and wherein the mononitrile reactant and monoadduct recovered from said pyrolysis effluent is recycled to the step of reacting said mononitrile reactant with said monoadduct.

16. A process in accordance with claim 15 wherein said decomposition product also comprises said olefinic hydrocarbon compound and further comprising reacting said mononitrile compound with said olefinic hydrocarbon compound to produce monoadduct utilized in said step of reacting said mononitrile reactant with said monoadduct, and recycling the olefinic hydrocarbon compound recover from said pyrolysis effluent to the step of reacting said mononitrile compound with said olefinic hydrocarbon compound.

17. A process in accordance with claim 1 wherein at least about 90 weight percent of said at least one undesired compound is not distillable at 0.0133 kPa and 320° C.

18. A process of recovering desirable materials from the heavies fraction of the crude reaction product which has been produced by reacting (a) at least one olefinically unsaturated mononitrile reactant and (b) at least one monoadduct of an olefinic hydrocarbon compound and an olefinically unsaturated mononitrile compound under reaction conditions suitable to produce at least one desired olefinically unsaturated dinitrile product and at least one undesired compound having a higher boiling point than said at least one desired olefinically unsaturated dinitrile product, each of said olefinically unsaturated mononitrile reactant and said olefinically unsaturated mononitrile compound containing a cyano group attached to a carbon atom adjacent and doubly bonded to a carbon atom which is attached to at least one hydrogen atom, said olefinic hydrocarbon compound having at least one olefinic linkage having joined to one of the doubly bonded carbons thereof a carbon atom having at least one hydrogen atom attached thereto; the resulting crude reaction product having been separated into a first fraction comprising said at least one desired olefinically unsaturated dinitrile product and a heavies fraction comprising said at least one undesired compound; which comprises subjecting said heavies fraction to pryolysis conditions to decompose at least a portion of said at least one undesired compound to therby produce a decomposition product comprising at least one of said at least one olefinically unsaturated mononitrile reactant, said at least one monoadduct, said olefinic hydrocarbon compound and said olefinically unsaturated mononitrile compound; and recovering said decomposition product from the resulting pyrolysis effluent.

19. A process in accordance with claim 18 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

20. A process in accordance with claim 19 wherein said mononitrile reactant is acrylonitrile, said mononitrile compound is acrylonitrile and said olefinic hydrocarbon compound is isobutylene.

21. A process in accordance with claim 19 wherein each of said at least one olefinic hydrocarbon compound, said at least one olefinically unsaturated mononitrile reactant and said at least one olefinically unsaturated mononitrile compound is free of acetylenic unsaturation and has from 3 to 18 carbon atoms per molecule with from 1 to 2 ethylenically unsaturated, nonconjugated double bonds as the sole aliphatic unsaturation;

wherein each said olefinic hydrocarbon compound is represented by the formula $R'_2C=CR'—CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound is represented by the formula $RCH=CR—CN$ wherein each R is independently selected from the group consisting of hydrogen and hydrocarbyl radicals.

22. A process in accordance with claim 21 wherein said reaction conditions comprise:

a reaction temperature in the range of about 100° to about 500° C., a reaction pressure in the range of about atmospheric pressure to about 100,000 psig, and a reaction time in the range of about two minutes to about 48 hours for a batch reaction or a liquid hourly space velocity in the range of about 0.05 to about 20 for a continuous reaction.

23. A process in accordance with claim 22 wherein said crude reaction product is separated into said first fraction and said heavies fraction at a temperature in the range of about 25° to about 250° C. and a pressure in the range of about 0.01 kPa to about 110 kPa.

24. A process in accordance with claim 23 wherein said mononitrile reactant is acrylonitrile, said mononitrile compound is acrylonitrile and said olefinic hydrocarbon compound is isobutylene.

25. A process in accordance with claim 14 wherein said reaction conditions comprise:

a reaction temperature in the range of about 100° C. to about 500° C., a reaction pressure in the range of about atmospheric pressure to about 100,000 psig, and a reaction time in the range of about two minutes to about 48 hours for a batch reaction or a liquid hourly space velocity in the range of about 0.05 to about 20 for a continuous reaction.

26. A process in accordance with claim 25 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

27. A process in accordance with claim 26 wherein said reaction effluent is separated into said first and second fractions at a temperature in the range of about 25° to about 250° C. and a pressure in the range of about 0.01 kPa to about 110 kPa.

28. A process in accordance with claim 26 wherein said mononitrile reactant is acrylonitrile, said mononitrile compound is acrylonitrile and said olefinic hydrocarbon compound is isobutylene.

* * * * *